United States Patent
Busolli et al.

(10) Patent No.: US 8,629,152 B2
(45) Date of Patent: *Jan. 14, 2014

(54) PROCESSES FOR THE PREPARATION OF LYOPHILIZED PHARMACEUTICALLY ACCEPTABLE SALTS OF PEMETREXED DIACID

(75) Inventors: Jonathan Busolli, Carisio (IT); Nicola Diulgheroff, Turin (IT); Moran Pirkes, Jerusalem (IL); Alessandro Pontiroli, S. Maria della Versa (IT); Marco Villa, Milan (IT); Zvi Harel, Kfar Saba (IL)

(73) Assignee: Sicor, Inc., Irvine, CA (US)

( * ) Notice: Subject to any disclaimer, the term of this patent is extended or adjusted under 35 U.S.C. 154(b) by 1567 days.

This patent is subject to a terminal disclaimer.

(21) Appl. No.: 11/893,234

(22) Filed: Aug. 14, 2007

(65) Prior Publication Data

US 2008/0139810 A1 Jun. 12, 2008

Related U.S. Application Data

(60) Provisional application No. 60/847,291, filed on Sep. 25, 2006, provisional application No. 60/855,139, filed on Oct. 30, 2006, provisional application No. 60/880,179, filed on Jan. 11, 2007, provisional application No. 60/958,326, filed on Jul. 2, 2007, provisional application No. 60/837,303, filed on Aug. 14, 2006, provisional application No. 60/860,557, filed on Nov. 21, 2006, provisional application No. 60/837,637, filed on Aug. 15, 2006, provisional application No. 60/860,554, filed on Nov. 21, 2006, provisional application No. 60/880,178, filed on Jan. 11, 2007, provisional application No. 60/958,213, filed on Jul. 3, 2007, provisional application No. 60/839,551, filed on Aug. 22, 2006, provisional application No. 60/845,031, filed on Sep. 14, 2006, provisional application No. 60/899,928, filed on Feb. 6, 2007, provisional application No. 60/936,553, filed on Jun. 20, 2007, provisional application No. 60/958,413, filed on Jul. 5, 2007.

(51) Int. Cl.
*A61K 31/519* (2006.01)
*C07D 487/04* (2006.01)

(52) U.S. Cl.
USPC ........................................... 514/265.1

(58) Field of Classification Search
USPC ........................................ 544/280; 514/265.1
See application file for complete search history.

(56) References Cited

U.S. PATENT DOCUMENTS

| | | | |
|---|---|---|---|
| 5,344,932 A | 9/1994 | Taylor | |
| 5,416,211 A | 5/1995 | Barnett et al. | |
| 6,262,262 B1 * | 7/2001 | Kjell | 544/280 |
| 7,138,521 B2 | 11/2006 | Chelius et al. | |
| 2003/0216416 A1 | 11/2003 | Chelius et al. | |
| 2006/0217392 A1 * | 9/2006 | Anilkumar et al. | 514/253.01 |
| 2007/0116729 A1 * | 5/2007 | Palepu | 424/400 |

FOREIGN PATENT DOCUMENTS

| | | |
|---|---|---|
| EP | 0 432 677 A1 | 6/1991 |
| EP | 0 434 426 A1 | 6/1991 |
| WO | WO-01/14379 A2 | 3/2001 |
| WO | WO 2008/124485 A2 | 10/2008 |

OTHER PUBLICATIONS

FDA website (http://www.accessdata.fda.gov/drugsatfda_docs/label/2009/021462s0211bl.pdf), downloaded Sep. 9, 2010, pp. 1-23.*
Physicians' Desk Reference, 1722-1728 (60th ed. 2006).
Barnett, Charles, et al., "A Practical Synthesis of Multitargeted Antifolate LY231514," *Organic Process Research & Development*, 3(3): 184-188 (1999).
U.S. Pharmacopeia, 387-389 (30th ed. 2007).
Kjell, Douglas P., et al., "Determination of the Source of the N-Methyl Impurity in the Synthesis of Pemetrexed Disodium Heptahydrate," *Organic Process Research and Development*, 9(6): 738-742 (2005).
International Conference on Harmonisation of Technical Requirements for Registration of Pharmaceuticals for Human Use, ICH Harmoniszed Tripartite Guideline: Good Manufacturing Practice Guide for Active Pharmaceutical Ingredients Q7 (Current Step 4 version, Nov. 10, 2000) (available at http://www.ich.org/LOB/media/MEDIA433.pdf, last visited Dec. 21, 2007).

* cited by examiner

*Primary Examiner* — Susanna Moore
(74) *Attorney, Agent, or Firm* — Arent Fox LLP

(57) ABSTRACT

Provided are processes for the preparation of lyophilized pharmaceutically acceptable salts of pemetrexed diacid, in particular, pemetrexed disodium salt, directly from pemetrexed diacid or salts thereof, i.e., without isolating the obtained pemetrexed salt prior to lyophilizing it.

18 Claims, No Drawings

PROCESSES FOR THE PREPARATION OF LYOPHILIZED PHARMACEUTICALLY ACCEPTABLE SALTS OF PEMETREXED DIACID

CROSS-REFERENCE TO RELATED APPLICATIONS

This application claims the benefit of U.S. provisional application Ser. Nos. 60/847,291, filed Sep. 25, 2006; 60/855, 139, filed Oct. 30, 2006; 60/880,179, filed Jan. 11, 2007; 60/958,326, filed Jul. 2, 2007; 60/837,303, filed Aug. 14, 2006; 60/860,557, filed Nov. 21, 2006; 60/837,637, filed Aug. 15, 2006; 60/860,554, filed Nov. 21, 2006; 60/880,178, filed Jan. 11, 2007; 60/958,213, filed Jul. 3, 2007; 60/839,551, filed Aug. 22, 2006; 60/845,031, filed Sep. 14, 2006; 60/899, 928, filed Feb. 6, 2007; 60/936,553, filed Jun. 20, 2007; and 60/958,413, filed Jul. 5, 2007, hereby incorporated by reference.

FIELD OF THE INVENTION

The invention is directed to processes for the preparation of lyophilized pharmaceutically acceptable salts of pemetrexed diacid, in particular, pemetrexed disodium salt, directly from pemetrexed diacid or salts thereof, i.e., without isolating the obtained pemetrexed salt prior to lyophilizing it.

BACKGROUND OF THE INVENTION

Compounds known to have antifolate activity are well recognized as chemotherapeutic agents for the treatment of cancer. In particular, compounds in the folic acid family have various activities at the enzymatic level as they inhibit such enzymes as dehydrofolate reductase, folate polyglutamate synthetase, glycinamide ribonucleotide formyltransferase and thymidylate synthetase.

A series of 4-hydroxypyrrolo[2,3-d]pyrimidine-L-glutamic acid derivatives have been disclosed, for example in EP 0434426, and shown to be particularly useful antifolate drugs, among them, pemetrexed disodium heptahydrate of formula I.

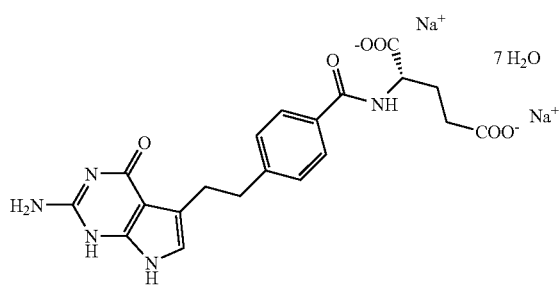

I

Pemetrexed disodium salt heptahydrate is marketed by Eli Lilly and Company under the trade name ALIMTA® as a sterile lyophilized powder for intravenous administration. This member of the folic acid family has been approved for treatment of malignant pleural mesothelioma and for second-line treatment of non small cell lung cancer. See *Physicians' Desk Reference*, 60th ed., pp. 1722-1728 (2006). The commercial product is reported to be a lyophilized powder of heptahydrate pemetrexed disodium and mannitol.

U.S. Pat. No. 7,138,521 discloses crystalline pemetrexed disodium heptahydrate. This heptahydrate form is prepared from N-[4-[2-(2-Amino-4,7-dihydro-4-oxo-3H-pyrrolo[2,3-d]pyrimidin-5-yl)ethyl]benzoyl]L-glutamic acid diethylester p-toluenesulfonic acid salt, which is saponified at a pH of between 2.5 to 3.5 to give N-[4-[2(2-amino-4,7-dihydro-4-oxo-1H-pyrrolo[2,3-d]pyrimidin-5-yl)ethyl]benzoyl]-L-glutamic acid ("pemetrexed diacid"), of the following Formula II:

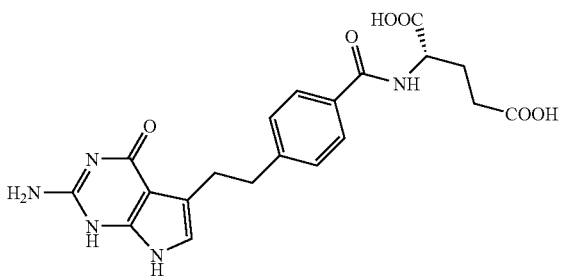

Pemetrexed diacid

The pemetrexed diacid is isolated as a wet cake and then combined with 2 to 3 equivalents of sodium hydroxide at a pH of between 7 and 9. The resulting pemetrexed disodium heptahydrate is then isolated from the reaction mixture by precipitation using acetone. The isolated pemetrexed disodium heptahydrate is then used to prepare the pharmaceutical composition.

International PCT publication WO 01/14379 discloses crystalline hydrated pemetrexed disodium and methods for preparing it from a carboxy-protected N-[4-[2-(2-amino-4,7-dihydro-4-oxo-3H-pyrrolo[2,3-d]pyrimidin-5-yl)ethyl]benzoyl]L-glutamic acid. The method includes reacting the carboxy-protected pemetrexed diacid with sodium hydroxide to obtain the pemetrexed disodium, without the need to pass through and to isolate pemetrexed diacid, which is stated to be "highly toxic" and to "requir[e] special handling measures and equipment." The obtained pemetrexed disodium is then used to prepare the pharmaceutical composition.

There is a need in the art for a method to produce the lyophilized disodium salt of pemetrexed diacid directly from pemetrexed diacid, i.e., without isolating the disodium salt of pemetrexed diacid.

SUMMARY OF THE INVENTION

In one embodiment, the invention encompasses a process for preparing a lyophilized pharmaceutically acceptable salt of pemetrexed comprising: combining pemetrexed diacid or a salt thereof, an agent capable of forming a pharmaceutically acceptable salt of pemetrexed, and a solvent comprising water or a mixture of water and a solvent suitable for lyophilization to obtain a mixture comprising a pharmaceutically acceptable salt of pemetrexed; and removing the solvent by lyophilization to obtain a lyophilized pharmaceutically acceptable salt of pemetrexed; wherein the pharmaceutically acceptable salt of pemetrexed is not isolated prior to the lyophilization process; and the pharmaceutically acceptable salt of pemetrexed is a di-base-addition salt of pemetrexed, with the proviso that the di-base-addition salt of pemetrexed is not the same as the starting pemetrexed diacid salt.

DETAILED DESCRIPTION OF THE INVENTION

The invention meets a need in the art by providing a method of preparing a lyophilized pharmaceutically acceptable salt of pemetrexed, especially, the disodium salt, directly from pemetrexed diacid or a salt thereof without the need for isolation of the obtained pharmaceutically acceptable salt of pemetrexed, prior to lyophilizing it. The obtained lyophilized pharmaceutically acceptable salt of pemetrexed can be used as the formulated product or can be combined with excipients during formulation.

The lyophilized pharmaceutically acceptable salt of pemetrexed is preferably substantially pure. Not isolating the obtained pharmaceutically acceptable salt prior to lyophilizing is advantageous because pemetrexed is subject to degradation over time. Hence, there is an advantage to reducing the number of process steps involved in manufacturing the product because reducing the number of process steps reduces the potential for degradation.

As used herein, unless otherwise defined, the term "substantially pure," when referring to a pharmaceutically acceptable salt of pemetrexed, relates to a pharmaceutically acceptable salt of pemetrexed having a purity of 99.6% or more. Preferably, the pharmaceutically acceptable salt of pemetrexed has a purity of 99.7% or more, more preferably 99.8% or more and most preferably 99.9% or more. The purity can be measured by area % units by HPLC.

In one embodiment, the invention encompasses a process for preparing a lyophilized pharmaceutically acceptable salt of pemetrexed comprising: combining pemetrexed diacid or a salt thereof, an agent capable of forming a pharmaceutically acceptable salt of pemetrexed, and a solvent comprising water or a mixture of water and a solvent suitable for lyophilization to obtain a mixture comprising a pharmaceutically acceptable salt of pemetrexed; and removing the solvent by lyophilization to obtain a lyophilized pharmaceutically acceptable salt of pemetrexed; wherein the pharmaceutically acceptable salt of pemetrexed is not isolated prior to the lyophilization process; and the pharmaceutically acceptable salt of pemetrexed is a di-base-addition salt of pemetrexed, with the proviso that the di-base-addition salt of pemetrexed is not the same as the starting pemetrexed diacid salt.

As used herein, unless otherwise, defined, an "agent capable of forming a pharmaceutically acceptable salt of pemetrexed" refers to an agent that is capable of forming a base-addition salt of pemetrexed. Base-addition salts include, but are not limited to, alkali or alkaline earth metal salts, such as sodium, potassium, lithium, and calcium salts.

Preferably, the agent capable of forming a pharmaceutically acceptable salt of pemetrexed is an alkali (preferably sodium) or alkaline earth metal hydroxide, carbonate, phosphate, or sulfate. More preferably, the agent capable of forming a pharmaceutically acceptable salt of pemetrexed is an alkali or alkaline earth metal hydroxide, and most preferably sodium hydroxide.

The starting pemetrexed diacid salt can be an acid-addition salt or a base-addition salt. The salt can be a di salt or a mono salt. Preferably the starting pemetrexed diacid salt is a mono salt.

As used herein, unless otherwise defined, the term "mono," with reference to a pemetrexed diacid salt, refers to a salt having only one counter cation or anion. When the salt is basic the counter cation is originated from a base. When the salt is acidic, the counter anion is originated from an acid.

Examples of mono base-addition salts of pemetrexed diacid include, but are not limited to, alkali or alkaline earth metal salts, such as sodium, potassium, lithium, and calcium salts. Preferably, the mono base-addition salt is a sodium salt of the following formula:

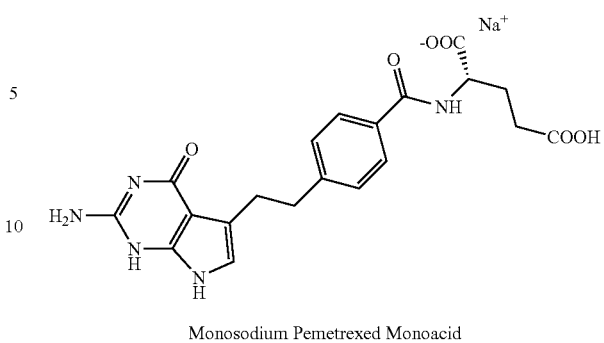

Monosodium Pemetrexed Monoacid

Examples of mono acid-addition salts of pemetrexed diacid include, but are not limited to, HBr, HCl, $H_2SO_4$, $H_3PO_4$, and $CH_3SO_3H$ salts. Preferably, the mono acid-addition salt is a HCl salt of the following formula:

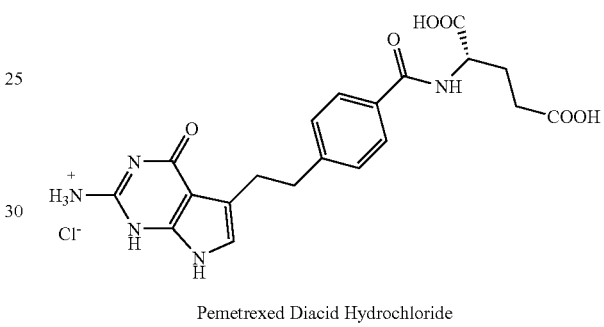

Pemetrexed Diacid Hydrochloride

As used herein, unless otherwise defined, the term "di," with reference to a pemetrexed diacid salt, refers to a salt having two counter cations. Preferably, the di-salt is a di-base-addition salt where these cations are originated from at least one base.

Preferably, the di-salt of pemetrexed diacid is selected from a group consisting of sodium, potassium, lithium, and calcium. More preferably, the di-salt is a disodium salt.

The purity of the starting pemetrexed diacid or salt thereof may affect the quality of the obtained lyophilized pharmaceutically acceptable salt of pemetrexed. Hence, the starting pemetrexed diacid or salt thereof is preferably pure. As used herein, unless otherwise defined, the term "pure" in the context of pemetrexed diacid or a salt thereof refers to pemetrexed diacid or a salt thereof with a purity of at least about 98%. Preferably, the pemetrexed diacid or salt thereof has a purity of at least about 99%, and more preferably, is substantially pure. The purity of pemetrexed diacid or salt thereof can be measured by area % units by HPLC.

The pemetrexed diacid may be obtained by any method known to a skilled artisan. For example, the pemetrexed diacid may be prepared according to the process disclosed in Org. Proc. Res. Dev. 2005, pp. 738-742 or by the method disclosed in co-pending U.S. application Ser. No. 11/893,299, filed Aug. 14, 2007, entitled "Highly Pure Pemetrexed Diacid and Processes for the Preparation Thereof," as well as U.S. provisional Application Nos. 60/837,637, filed Aug. 15, 2006; 60/860,554, filed Nov. 21, 2006; 60/880,178, filed Jan. 11, 2007; and 60/958,213, filed Jul. 3, 2007, all of which are incorporated herein by reference. The method comprises crystallizing pemetrexed diacid from a mixture comprising a solvent selected from the group consisting of an amide, a pyrrolidinone, a sulfoxide, and mixtures thereof, and an anti-solvent selected from the group consisting of an alcohol, an ester, a ketone, water, a halogenated hydrocarbon, an aromatic hydrocarbon, an ether, and mixtures thereof, wherein the starting pemetrexed diacid has a purity of at least about 98%.

In a preferred embodiment, initially, the pemetrexed diacid or salt thereof is combined with the solvent to obtain a first mixture. Preferably, the solvent is water. When a mixture of water and a solvent suitable for lyophilization is used, the solvent suitable for lyophilization may include, but is not limited to, tert-butanol, dimethylsulfoxide, or 1,4-dioxane. Preferably, the solvent suitable for lyophilization is tert-butanol.

The first mixture is then admixed with an alkali or alkaline earth metal hydroxide to obtain the mixture comprising the pharmaceutically acceptable salt of pemetrexed, and optionally a salt generated from a reaction between the alkali or alkaline earth metal hydroxide and a mono acid-addition salt of pemetrexed diacid, depending on the starting material. When the starting material is a mono acid-addition salt of pemetrexed diacid, the mixture comprising the pharmaceutically acceptable salt of pemetrexed also includes a salt, which is also a pharmaceutically acceptable salt, generated from a reaction between the alkali or alkaline earth metal hydroxide and the mono acid-addition salt of pemetrexed diacid.

Preferably, the alkali or alkaline earth metal hydroxide is NaOH, KOH, LiOH, or $Ca(OH)_2$, and more preferably, NaOH. Accordingly, the salt generated from the alkali or alkaline earth metal hydroxide and the mono acid-addition salt of pemetrexed diacid is preferably, NaBr, NaCl, KBr, KCl, LiBr, LiCl, $CaBr_2$, or $CaCl_2$.

Preferably, the alkali or alkaline earth metal hydroxide is added to the first mixture. Preferably, the mixture is a solution.

Typically, to obtain the pharmaceutically acceptable salt of pemetrexed from pemetrexed diacid and salt thereof, at least about 1 mole equivalent of alkali or alkaline earth metal hydroxide per mole equivalent of the starting pemetrexed diacid or salt thereof is used. Preferably, the alkali hydroxide is used in an amount of about 1 to about 3 mole equivalents per mole equivalent of the starting pemetrexed diacid or salt thereof.

The alkali hydroxide may be in solution or solid form. Preferably, the alkali or alkaline earth metal hydroxide is in the form of an aqueous solution. Preferably, the aqueous solution of the alkali or alkaline earth metal hydroxide is a standard solution. As used herein, unless otherwise defined, the term "standard solution" refers to a solution having a known concentration, where the concentration is determined by various methods known to a skilled artisan, such as titration with acids. Preferably, the standard solution of the alkali or alkaline earth metal hydroxide has a concentration of about 0.5 M to about 4 M, more preferably, of about 2 M.

Preferably, admixing the first mixture and the alkali or alkaline earth metal hydroxide solution is performed at a temperature of about 1° C. to about 100° C., more preferably at about 10° C. to about 60° C., and most preferably at about 15° C. to about 40° C.

As a skilled artisan will appreciate, complete dissolution or a stable pH value of about 7.0 to 7.5, or, more preferably, 7.1 to 7.2, is an indication that the reaction has completed.

The process for preparing lyophilized pharmaceutically acceptable salt of pemetrexed may further comprise a process of adjusting the pH to obtain a pH of about 7.0 to about 10.0, preferably, of about 7.0 to about 9.0, more preferably, of about 7.0 to about 8.0, and most preferably, of about 7.0 to about 7.5, prior to lyophilizing the solution comprising the pharmaceutically acceptable salt of pemetrexed. The pH can be adjusted by admixing the solution comprising the pharmaceutically acceptable salt of pemetrexed, and optionally the additional pharmaceutically acceptable salt described before, with alkali hydroxide or with any one of the starting materials, i.e., pemetrexed diacid, and its salts, depending on the pH of the solution. Typically, the pH measurement is done by using a pH-meter.

As mentioned before, the formulated pemetrexed disodium can be prepared by lyophilizing the salt without excipients. Optionally, a dispersing agent may be added to the mixture before removing the solvent. Preferably, the dispersing agent is a sugar such as lactose, fructose or mannitol. Preferably, the sugar is mannitol. Preferably, the dispersing agent is present in an equimolar amount in weight relative to the amount of the pharmaceutically acceptable salt of pemetrexed.

Although the pharmaceutically acceptable salt of pemetrexed is not isolated during the process and thus not purified, the lyophilized salt thus obtained is preferably pure. More preferably, the lyophilized salt thus obtained is substantially pure.

The lyophilized pharmaceutically acceptable salt of pemetrexed obtained by the above-described process may be formulated into pharmaceutical compositions comprising at least one lyophilized pharmaceutically acceptable salt of pemetrexed and, optionally, at least one pharmaceutically acceptable excipient. Suitable excipients include, but are not limited to, diluents, carriers, fillers, bulking agents, binders, disintegrants, disintegration inhibitors, absorption accelerators, wetting agents, lubricants, glidants, surface active agents, flavoring agents, and the like. Selection of excipients and the amounts to use can be readily determined by an experienced formulation scientist in view of standard procedures and reference works known in the art.

The pharmaceutical compositions can be formulated into a solid or a liquid dosage form for administration to a patient. Dosage forms include, but are not limited to, tablets, capsules, powders, syrups, suspensions, emulsions, injection preparations, and the like. Preferably, the dosage form is an injection preparation.

The pharmaceutical compositions comprising the lyophilized pharmaceutically acceptable salts of pemetrexed obtained by the above-described process may be used in methods of treating malignant pleural mesothelioma or non small cell lung cancer. In particular, the method may comprise treating malignant pleural mesothelioma or non small cell lung cancer by administering a therapeutically effective amount of a pharmaceutical composition comprising at least one lyophilized pharmaceutically acceptable salt of pemetrexed obtained by the process of the present invention and, optionally, at least one pharmaceutically acceptable excipient to a patient in need thereof.

Having described the invention with reference to certain preferred embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

HPLC Method for Monitoring the Purity of Pemetrexed Diacid

| Column & Packing: | GEMINI C18; 110 Å; 3 μm; 150 × 4.6 mm (PHENOMENEX P.N. 00F-4439-EO) or equivalent |
|---|---|
| Eluent A: | 3 mL of TFA in 1000 mL of water |
| Eluent B: | Acetonitrile |
| Gradient | Time (min) / % Eluent A / % Eluent B |
| | 0 / 85 / 15 |
| | 2 / 85 / 15 |
| | 30 / 40 / 60 |
| | 35 / 40 / 60 |
| | 36 / 85 / 15 |
| Run time | 35 minutes |
| Equilibrium time: | 5 minutes |
| Flow Rate: | 1.0 mL/min. |
| Detector: | UV at 254 nm |
| Column temperature: | 25° C. |
| Injection | 5 μl |
| Diluent | $NaH_2PO_4$ 4 g/L in water at pH = 7.5 |

Detection Limit: 0.003% area.
Mobile phase composition and flow rate may be varied in order to achieve the required system suitability.

Example 1

Lyophilized N-[4-[2-(2-amino-4,7-dihydro-4-oxo-1H-pyrrolo[2,3-d]pyrimidin-5-yl)ethyl]benzoyl]-L-glutamic acid disodium salt 5 grams of N-[4-[2-(2-amino-4,7-dihydro-4-oxo-1H-pyrrolo[2,3-d]pyrimidin-5-yl)ethyl]benzoyl]-L-glutamic acid (purity 99.6% by HPLC) was dissolved in 1 L of distilled water and 11.698 ml of a 2.0 M solution of sodium hydroxide was added to the solution. Mannitol (10 g) was added to the solution and dissolved. The solution was then filtered through a bacterial filter and dried in a freeze-drier to afford the title compound as a white solid in mixture with mannitol (15.5 g, purity 99.6% area by HPLC).

Example 2

Lyophilized N-[4-[2-(2-amino-4,7-dihydro-4-oxo-1H-pyrrolo[2,3-d]pyrimidin-5-yl)ethyl]benzoyl]-L-glutamic acid disodium salt 2.5 grams of N-[4-[2-(2-amino-4,7-dihydro-4-oxo-1H-pyrrolo[2,3-d]pyrimidin-5-yl)ethyl]benzoyl]-L-glutamic acid (purity 99.6% by HPLC) were dissolved in 0.5 L of distilled water with the addition of 5.849 mL of a 2.0M standard solution of sodium hydroxide. The pH of the solution was adjusted to 7.14 by adding a diluted solution of sodium hydroxide in water and a suspension of N-[4-[2-(2-amino-4,7-dihydro-4-oxo-1H-pyrrolo[2,3-d]pyrimidin-5-yl)ethyl]benzoyl]-L-glutamic acid in the same solvent. The obtained solution was dried in a freeze-drier affording the title compound as a white solid (2.8 g, purity 99.6% area by HPLC). Acidimetric titrations of the final product confirmed the absence of residual sodium hydroxide and pemetrexed diacid.

Example 3

Lyophilized N-[4-[2-(2-amino-4,7-dihydro-4-oxo-1H-pyrrolo[2,3-d]pyrimidin-5-yl)ethyl]benzoyl]-L-glutamic acid disodium salt 2.5 grams of N-[4-[2-(2-amino-4,7-dihydro-4-oxo-1H-pyrrolo[2,3-d]pyrimidin-5-yl)ethyl]benzoyl]-L-glutamic acid (purity 99.6% HPLC) were dissolved in a mixture of 0.3 L of distilled water and 0.2 L of t-butanol with the addition of 5.849 mL of a 2.0M standard solution of sodium hydroxide in water. The pH of the solution was adjusted to 7.14 by adding a diluted solution of sodium hydroxide in water and a suspension of N-[4-[2-(2-amino-4,7-dihydro-4-oxo-1H-pyrrolo[2,3-d]pyrimidin-5-yl)ethyl]benzoyl]-L-glutamic acid in the same solvent. The obtained solution was dried in a freeze-drier affording the title compound as a white solid (2.7 g, purity 99.6% area by HPLC). Acidimetric titrations of the final product can be used to confirm the absence of residual sodium hydroxide and pemetrexed diacid.

Example 4

Lyophilized N-[4-[2-(2-amino-4,7-dihydro-4-oxo-1H-pyrrolo[2,3-d]pyrimidin-5-yl)ethyl]benzoyl]-L-glutamic acid disodium salt 5 grams of N-[4-[2-(2-amino-4,7-dihydro-4-oxo-1H-pyrrolo[2,3-d]pyrimidin-5-yl)ethyl]benzoyl]-L-glutamic acid monosodium salt (purity 99.7% by HPLC) are dissolved in 1 L of distilled water and 5.563 ml of a 2.0 M solution of sodium hydroxide is added to the solution. Mannitol (10 g) is then added to the solution and dissolved. The solution is then filtered through a bacterial filter and dried in a freeze-drier to afford the title compound as a white solid in mixture with mannitol (15.2 g, purity 99.7% area by HPLC).

Example 5

Lyophilized N-[4-[2-(2-amino-4,7-dihydro-4-oxo-1H-pyrrolo[2,3-d]pyrimidin-5-yl)ethyl]benzoyl]-L-glutamic acid disodium salt 5 grams of N-[4-[2-(2-amino-4,7-dihydro-4-oxo-1H-pyrrolo[2,3-d]pyrimidin-5-yl)ethyl]benzoyl]-L-glutamic acid hydrochloride (purity 99.4% by HPLC) is dissolved in 1 L of distilled water and 16.168 ml of a 2.0 M solution of sodium hydroxide is added to the solution. Mannitol (10 g) was then added to the solution and dissolved. The solution is then filtered through a bacterial filter and dried in a freeze-drier to afford the title compound as a white solid in mixture with mannitol and sodium chloride (15.6 g, HPLC purity 99.4% area by HPLC).

Example 6

Purification of N-[4-[2-(2-Amino-4,7-dihydro-4-oxo-1H-pyrrolo[2,3-d]pyrimidin-5-yl)ethyl]benzoyl]-L-glutamic acid A flask was charged with N-[4-[2-(2-amino-4,7-dihydro-4-oxo-1H-pyrrolo[2,3-d]pyrimidin-5-yl)ethyl]benzoyl]-L-glutamic acid (99.07% HPLC purity) (2.25 g) and dimethylsulfoxide (6.75 ml), heated to 45° C. and stirred until complete dissolution. Absolute ethanol (20.25 ml) was then added drop wise in about 2 hours, the obtained suspension was stirred for 1 hour at 45° C. and then cooled to 30° C. in about 2 hours. The suspension was filtered and the solid was washed with water (20.25 ml). The wet solid was slurried at 45° C. in absolute ethanol (20.25 ml) for one hour, cooled to 30° C. and filtered. After drying at 40° C. under vacuum (18 mbar) for about 16 hours, the title compound was obtained in 99.81% purity (HPLC).

What is claimed is:

1. A process for preparing a formulated pemetrexed disodium composition comprising:
   a) combining:
      (i) pemetrexed diacid or a salt thereof,
      (ii) NaOH,
      (iii) a solvent comprising water or a mixture of water and a solvent suitable for lyophilization, and
      (iv) a dispersing agent to obtain a mixture comprising pemetrexed disodium; and
   b) removing the solvent by lyophilization to obtain a formulated pemetrexed disodium composition, wherein the pemetrexed disodium is not isolated prior to the lyophilization process, with the proviso that the pemetrexed diacid salt of step a) i) is not pemetrexed disodium.

2. The process of claim 1, wherein the pemetrexed diacid salt of step a) i) is an acid-addition salt.

3. The process of claim 2, wherein the acid-addition salt is a mono salt.

4. The process of claim 3, wherein the mono salt is a HBr, HCl, $H_2SO_4$, $H_3PO_4$, or $CH_3SO_3H$ salt.

5. The process of claim 1, wherein the pemetrexed diacid salt of step a) i) is a base-addition salt.

6. The process of claim 5, wherein the base-addition salt is a mono salt.

7. The process of claim 6, wherein the mono salt is an alkali or alkaline earth metal salt.

8. The process of claim 7, wherein the alkali or alkaline earth metal salt is a sodium, potassium, lithium, or calcium salt.

9. The process of claim 1, wherein the solvent suitable for lyophilization is tert-butanol, dimethylsulfoxide, or 1,4-dioxane.

10. The process of claim 1, wherein the solvent is water or a mixture of water and tert-butanol.

11. The process of claim 1, wherein the NaOH is present in an amount of at least about 1 mole equivalent per mole equivalent of pemetrexed diacid or salt thereof.

12. The process of claim 1, wherein the pemetrexed diacid or salt thereof is combined with the solvent to obtain a first mixture, prior to combining with the NaOH.

13. The process of claim 12, wherein the first mixture is combined with the NaOH at a temperature of about 1° C. to about 100° C.

14. The process of claim 1, further comprising adjusting the pH of the mixture comprising the pemetrexed disodium to about 7.0 to about 10.0 prior to removing the solvent by lyophilization.

15. The process of claim 14, wherein the pH is adjusted to about 7.0 to about 9.0.

16. The process of claim 14, wherein the pH is adjusted to about 7.0 to about 8.0.

17. The process of claim 16, wherein the dispersing agent is a sugar.

18. The process of claim 17, wherein the sugar is lactose, fructose, or mannitol.

* * * * *